United States Patent
Gutleb et al.

(10) Patent No.: US 11,655,442 B2
(45) Date of Patent: May 23, 2023

(54) CELL BIO-INCUBATOR WITH A VARIABLE INTERNAL PRESSURE

(71) Applicant: LUXEMBOURG INSTITUTE OF SCIENCE AND TECHNOLOGY (LIST), Esch-sur-Alzette (LU)

(72) Inventors: Arno Gutleb, Remich (LU); Tommaso Serchi, Kirsch-les-Sierck (FR); Mathieu Gerard, Rehon (FR)

(73) Assignee: LUXEMBOURG INSTITUTE OF SCIENCE AND TECHNOLOGY (LIST), Luxembourg (LU)

( * ) Notice: Subject to any disclaimer, the term of this patent is extended or adjusted under 35 U.S.C. 154(b) by 21 days.

(21) Appl. No.: 16/954,235

(22) PCT Filed: Dec. 31, 2018

(86) PCT No.: PCT/EP2018/086900
§ 371 (c)(1),
(2) Date: Jun. 16, 2020

(87) PCT Pub. No.: WO2019/129799
PCT Pub. Date: Jul. 4, 2019

(65) Prior Publication Data
US 2020/0339937 A1    Oct. 29, 2020

(30) Foreign Application Priority Data

Dec. 27, 2017   (LU) .................................... LU100595

(51) Int. Cl.
*C12M 1/42*     (2006.01)
*C12M 1/00*     (2006.01)
*C12M 1/34*     (2006.01)

(52) U.S. Cl.
CPC ............ *C12M 35/04* (2013.01); *C12M 29/14* (2013.01); *C12M 41/14* (2013.01); *C12M 41/40* (2013.01)

(58) Field of Classification Search
CPC ...... C12M 35/04; C12M 29/14; C12M 41/14; C12M 41/40
See application file for complete search history.

(56) References Cited

U.S. PATENT DOCUMENTS 3,607,659 A  *  9/1971  Bloomer ................ C12M 23/08
                                                     435/302.1
6,303,835 B1 * 10/2001  Shafer ..................... C07C 37/52
                                                     568/806

(Continued)

FOREIGN PATENT DOCUMENTS

DE          10030528 A1    1/2002
WO       2015138999 A1    9/2015

OTHER PUBLICATIONS

International Search Report for PCT/EP2018/086900 dated Mar. 18, 2019.

(Continued)

*Primary Examiner* — William H. Beisner
*Assistant Examiner* — Danielle B Henkel
(74) *Attorney, Agent, or Firm* — Sandberg Phoenix & von Gontard, PC

(57) ABSTRACT

A system for incubating one or more cells and/or organotypic cultures for biological investigation, in particular for toxicology assessment, comprising a bio-incubator and a pressure system fluidly connected with the bio-incubator. The pressure system is a cyclic gas pressure system configured for cyclically varying the gas pressure in the bio-incubator between a negative pressure and a positive pressure compared to the atmospheric pressure, so as to reproduce the pressure conditions in lungs of a living (Continued)

mammal. The system is remarkable in that the cyclic gas pressure system comprises a feedthrough with a pipe configured to deviate the air influx from the one or more cells and/or organotypic cultures.

19 Claims, 6 Drawing Sheets

(56) References Cited

U.S. PATENT DOCUMENTS

| | | | | |
|---|---|---|---|---|
| 8,865,460 | B2* | 10/2014 | Orr | C12M 25/14 |
| | | | | 435/305.2 |
| 2005/0002910 | A1* | 1/2005 | Wolfinbarger, Jr. | |
| | | | | C12N 5/0654 |
| | | | | 424/93.7 |
| 2005/0084956 | A1* | 4/2005 | Tamaoki | C12M 41/14 |
| | | | | 435/303.1 |
| 2009/0111180 | A1 | 4/2009 | Vilendrer et al. | |
| 2010/0311146 | A1* | 12/2010 | Auton | C12M 23/02 |
| | | | | 435/252.8 |
| 2015/0289501 | A1 | 10/2015 | Raredon et al. | |
| 2017/0072100 | A1* | 3/2017 | Gilbert | A61L 27/3691 |

OTHER PUBLICATIONS

Written Opinion for PCT/EP2018/086900 dated Mar. 18, 2019.
Adamson et al.; Assessment of an in vitro whole cigarette smoke exposure system: The Borgwaldt RM20S 8-syrginge smoking machine; Chemistry Central Journal, Biomed Central Ltd., Lo, vol. 5, No. 1, Aug. 26, 2011; p. 50.

\* cited by examiner

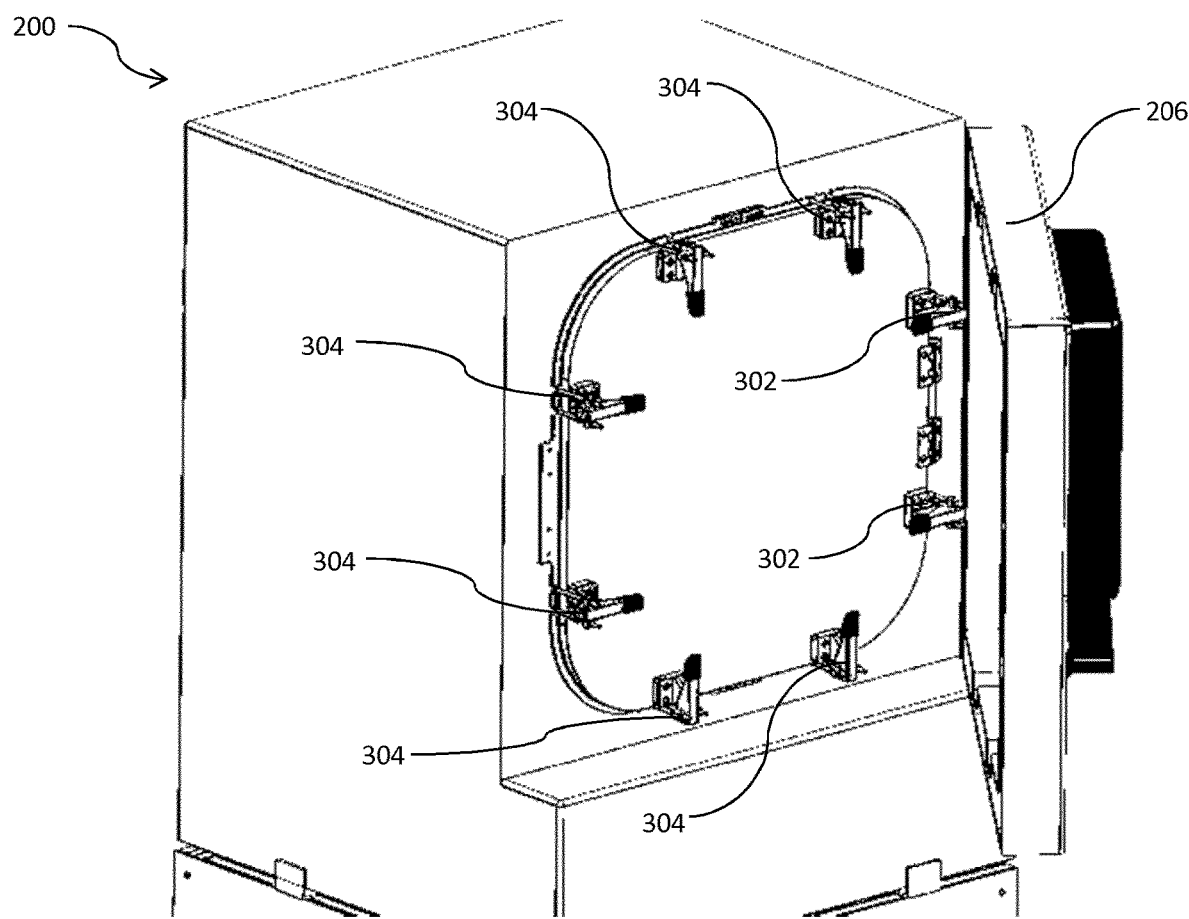
Fig. 8
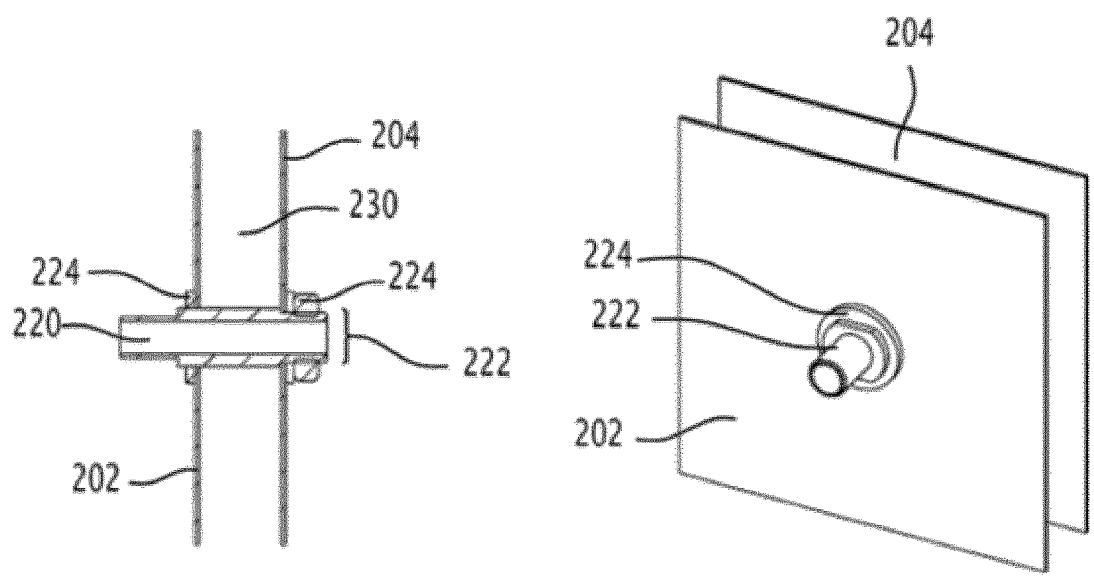
Fig. 9A          Fig. 9B

CELL BIO-INCUBATOR WITH A VARIABLE INTERNAL PRESSURE

CROSS-REFERENCE TO RELATED APPLICATIONS

The present invention is the US national stage under 35 U.S.C. § 371 of International Application No. PCT/EP2018/086900, which was filed on Dec. 31, 2018, and which claims the priority of application LU 100595 filed on Dec. 27, 2017, the content of which (text, drawings and claims) are incorporated here by reference in its entirety.

FIELD

The invention is directed to a system for incubation of one or more cells and/or organotypic cultures for biological investigation, in particular for toxicology assessment, from the point of view of the respiratory behaviour of mammals.

BACKGROUND

Nowadays, health risks linked to airborne pollutants are of increasing concern and should be taken into account during the development of new drugs and/or new treatments against allergy, asthma or any other respiratory diseases. The airborne pollutants are mainly caused by a massive industrialization, car pollution, natural phenomena such as volcanic eruption, fires, use of aerosol and/or spray in numerous situations, and/or in everyday production of dust and/or (nano)particles due to work with crumbly material.

In order to assess the risks linked to respiratory exposure of airborne contaminants in mammals, scientists are usually making use of in vivo models. The reason why in vivo models are used instead of in vitro models for respiratory toxicology is that at present there are no validated in vitro models for respiratory toxicology. Until a few years ago, the necessary technology to develop air liquid interface systems (that are compulsory for the development of relevant in vitro systems for toxicological applications) was not available. Such models have been developed in the last 10 years, but still, none of them has received official approval by regulatory bodies. Until that moment, they cannot be used for regulatory applications.

Moreover, the development of realistic models is quite complicated. There are many cell types involved and the tissue is organized in a 3D manner, making the design of the model even more complex. Another aspect is the exposure of the models. The technology to expose cells to reproducible and well characterized aerosols only came recently.

In addition, for many applications, it is easier to use in vivo models rather than in vitro systems.

In order to satisfy the 3R (Replacement, Reduction and Refinement) European directive (Directive 2010/63/EU of the European Parliament and of the Council of 22 Sep. 2010 on the protection of animals used for scientific purposes), the validation of an in vitro model is needed. Such an in vitro model should be ideally able to predict the in vivo toxicity with a sensitivity and accuracy equal to that of in vivo models.

The Vitrocell® exposure system has been successfully used for exposing in vitro lung models to gases, liquids or powders. The Vitrocell® exposure system has also been used for the exposure of chemicals (alone or in complex mixtures), nanoparticles and fibres. It allows the exposition of lung cells cultivated at the air-liquid-interface to aerosol of different foreign substances such as combustion exhaust, cosmetics, household chemicals, indoor/outdoor air analysis, industrial chemicals, pesticides, pharmaceuticals and/or tobacco smokes.

The mimicking of the physiological conditions and, in particular the mimicking of the respiratory system of a mammal, in order to study the behaviour of the lung cells, over exposition of foreign substances is still to be explored. Also, the study of the behaviour during the respiration of the lung cells already influenced with foreign substance(s) needs to be taken into consideration in order to provide more and more resembling physiological conditions in the study of the respiratory exposure.

The use of realistic in vitro models to study the effects of inhaled substances is of absolute importance. Nowadays several in vitro models exist with increasing complexity, i.e. from mono-cultures of lung epithelial cells grown in submerged conditions to advanced 3D multi-cellular models grown at the air-liquid-interface. However, none of these models take in consideration applying realistic conditions for what concerns the pressure shift to which the lung tissue is subjected in vivo. As cyclic pressure changes have the potential to strongly modulate the response of lung cells, it is of absolute importance to include realistic pressure conditions in in vitro studies, in order to obtain better predictive models.

This is necessary because the compression and the expansion of the chest change considerably the internal pressure of the lung allowing the respiratory acts. In quiet breathing, the intra-alveolar pressure changes, for the alveoli, from about −1-3 mbar to about +1-3 mbar compared to the atmospheric pressure. These variations, even in quiet breathing, are sufficient to be noticed by the lung cells. FIG. 1 shows an indication of the forces that occur during the respiration. A plot of the vital capacity (VC), i.e. the volume of air breathed out after the deepest inhalation, in function of the pressure is shown. The negative pressures correspond to the inhalation mode while the positive pressures correspond to the exhalation mode.

Prior art patent application document published US 2015/0317918 A1 relates to a respiration mimic device for accurately reflecting dynamic patterns of a human body changing according to respiration by reflecting actual respiration patterns of a patient. The device includes a lung copying unit which comprises a chamber having an interior space filled with fluid, a lung mimic to be contracted or expanded and accommodated at the interior space in the chamber, and a tumor mimic which is distributed in the lung mimic. It is a driving unit that is used for copying motion patterns of the lung according to actual respiration and for contracting or expanding the lung mimic. The driving unit includes a rod in which one end is coupled with the lung mimic. The driving unit is coupled to the abdomen copying unit in order to mimic the respiration, in particular the contraction and the expansion of the lung mimic. This model is basically a robotic model.

Prior art patent application document published US 2009/0111180 A1 discloses a bioreactor system for growing and conditioning tissues for research and implementation in a human or animal body. The bioreactor system is connected to a source of pressurized air for controlling the pressure inside the bioreactor. In this way, a hydrostatic state of stress can be applied to the tissue constructs in order to favour tissue development, mechanical properties of the tissues and tissue function. The pressurization system includes a pressure pack for creating a pressurized supply of air or other gas, which may be in the 80-150 psig range (i.e., 5 bar-10 bar).

Prior art patent application document published US 2015/0289501 A1 discloses a bioreactor for large-mammal lung tissues. The bioreactor is capable of hydraulic driven negative pressure and positive pressure perfusion and ventilation. The system provides a sterile environment for the decellularization, recellularization, and culture of an engineered human lung. In this system, the pressure system is a hydraulic pressure system. The drawback of the hydraulic pressure system is the use of one hydraulic fluid. The system can leak and subsequently contaminate that organ chamber that is connected to it. The cost of the material used in the hydraulic system is also relatively high.

Prior art patent application document published DE 100 30 528 A1 discloses a device for mechanically stretching a membrane on which cultured cells are applied, which has for effect to mechanically deform the cells that are applied on this membrane. The system, which is disclosed in this document concerns a deformation of the support of the cultured cells.

Prior art patent application document published WO 2015/138999 A1 discloses an airway organ bioreactor apparatus, used for ex vivo experiment. The lung is placed in a chamber, which is maintained under certain conditions of temperature, gas concentration and pressure. A pneumatic pressure control module is present and controls the inspiration phase (generation of negative pressure) and expiration phase (generation of a positive pressure) inside the lung chamber.

Prior art patent application document published US 2015/0289501 A1 discloses a bioreactor for large mammal lung tissue. Perfusion and ventilation (in a positive mode and a negative mode) is provided. In this document, the air influx is pushed in and expelled from the organ, since it relates to an in vitro model that mimics natural pulmonary tissues or to vascularized pulmonary tissues.

Prior art patent application document published US 2005/0084956 A1 discloses a multigas incubator as an incubator to incubate cultures such as cells or microbes. The main body of the incubator is made of an adiabatic box, with an adiabatic door. Heaters and humidification tray are arranged in the incubator.

It appears therefore that the art in the field of respiratory exposure system does not provide a system, which allows the lung cells to be studied in condition mimicking the mammal respiration. This is particularly important as the mechanical stress to which the cells are exposed during respiration (e.g. change of pressure and stretching) can modify the cellular metabolism so that they more/less sensitive to pollutants.

SUMMARY

The invention has for technical problem to alleviate at least one of the drawbacks present in the prior art. In particular, the present invention has for technical problem to provide a system which allows lung cells to survive in conditions which mimic the mammal respiration (in terms of min/max pressure and frequency of the respiratory act) with a simple, adjustable and convenient gas pressure system.

The first object of the invention is directed to a system for incubating one or more cells and/or organotypic cultures for biological investigation, in particular for toxicology assessment, comprising: (a) a bio-incubator with at least one orifice, and (b) a pressure system fluidly connected with the bio-incubator through the at least one orifice; the pressure system is a cyclic gas pressure system configured for cyclically varying the gas pressure in the bio-incubator between a negative pressure and a positive pressure compared to the atmospheric pressure, so as to reproduce the pressure conditions in lungs of a living mammal, wherein the orifice comprises a feedthrough. It is remarkable in that the feedthrough further comprises a pipe configured to deviate the air influx from the one or more cells and/or organotypic cultures.

In an exemplary embodiment, the pipe further comprises a fritted tip.

In an exemplary embodiment, the feedthrough is an air-tight traverse.

In an exemplary embodiment, the gas pressure in the bio-incubator is within a range comprised between −100 mbar and +100 mbar.

In an exemplary embodiment, the bio-incubator and the gas pressure system form a hermetically closed circuit.

In an exemplary embodiment, the hermetically closed circuit further comprises an openable connection to at least one gas source, in various instances a carbon dioxide source and/or an oxygen source.

In an exemplary embodiment, the bio-incubator further comprises at least one well adapted for cell cultures with a surface that is inferior or equal to 5 $cm^2$.

In an exemplary embodiment, the cyclic gas pressure system comprises a chamber with a volume that can be varied by an actuator, the chamber comprising at least one outlet in fluid connection with the bio-incubator.

In an exemplary embodiment, the system comprises a guiding assembly slidably mounted on the chamber and movable by the actuator, a wall of the chamber being coupled to the guiding assembly.

In an exemplary embodiment, the chamber is a bellow cylinder, in various instances a bellow cylinder comprising at least two bellows.

In an exemplary embodiment, the chamber is at least partially covered with heating elements, in various instances at least partially covered with silicone rubber heating elements.

In an exemplary embodiment, the actuator comprises a motor and a crank mechanism for reciprocally varying the volume of the chamber.

In an exemplary embodiment, the crank mechanism has an adjustable stroke and preferably comprises a crank rotably connected to a rod at an adjustable position along the crank.

In an exemplary embodiment, the bio-incubator comprises an opening delimited by a doorframe, a door for closing the opening, and a hermetic cover being mounted between the door and the opening, wherein the hermetic cover is designed for being air-tightly fixed by air-tight fixation elements to the doorframe, and wherein the bio-incubator further comprises a wall with an orifice configured to be in fluid connection with the cyclic gas pressure system.

In an exemplary embodiment, the bio-incubator further comprises a gauge needle.

In an exemplary embodiment, the door has a thickness comprised between 5 mm and 15 mm.

In an exemplary embodiment, the doorframe comprises a fasten mechanism.

In an exemplary embodiment, the hermetic cover comprises a fasten mechanism.

In an exemplary embodiment, the door further comprises a heating device, the heating device being in various instances disposed inside the door.

In an exemplary embodiment, the heating device is an electrical resistance.

In an exemplary embodiment, the hermetic cover further comprises a protruding portion designed for being air-tightly fixed by the air-tight fixation elements to the doorframe of the bio-incubator, in various instances through a counter-plate which is placed on the external wall of the bio-incubator at least partially around the doorframe, the counter-plate being more in various instances inserted into a recess disposed on the doorframe.

In an exemplary embodiment, the hermetic cover comprises a hermetic seal, preferably an O-ring seal, that fits with the doorframe of the door and the hermetic cover, the hermetic seal being preferably made of elastomer.

In an exemplary embodiment, the orifice traverses a zone between an external wall and an internal wall of the bio-incubator, and comprises an air-tight traverse fastened to the external wall and to the internal wall by air-tight fixation elements.

The second object of the invention relates to a device for analysing the effect of aerosol of nanoparticles on one or more cells, comprising a first system comprising exposure means for exposing aerosol to one or more cells, and a second system for incubating one or more cells and/or organotypic cultures for biological investigation, in particular for toxicology assessment. The device for analysing the effect of aerosol of nanoparticles on one or more cells is remarkable in that the second system is in accordance with the first object of the present invention.

According to an exemplary embodiment, the first system comprising exposure means for exposing aerosol to one or more cells is the Vitrocell® exposure system.

In general, the particular embodiments of each object of the invention are also applicable to other objects of the invention. To the extent possible, each object of the invention is combinable with other objects.

The invention is particularly interesting in that lung cells can be incubated in a condition similar to living conditions and can subsequently be studied. This similarity to the living conditions is obtained through a simple and cheap system. The modification of a commercially available device is very convenient and the coupling of this modified device with a reliable pressure system allows to mimic the living conditions, in particular to mimic the respiration system. This is very important for the studies of the behaviour of lung cells that have been formerly stressed through administration of foreign substances. The behaviour of such lung cells can thus be monitored by following the reaction of the lung cells that are placed under real respiratory conditions. The incubation of those lung cells is further achieved in the presence of a bio-incubator that presents all the necessary features required for studying the cells: maintenance of temperature, which is regulated (also in the part generating the pressure) in order to prevent the problem due to condensation, presence or not of humidity, possibility to adapt the wells adapted for cells culture in function of a biological culture.

The cell, cells or tissues, that are cultured into the bioincubator of the present invention can be submitted to various experimental conditions (difference and high variation of pressure, temperature, humidity, nutrient concentrations, etc.) during a certain amount of time (up to several weeks) without suffering from any damages.

One last advantage is that the system in accordance with the present invention can be coupled with known systems that are used for delivering aerosols. Therefore, in the field of the respiratory assessment, the development of an in vitro model mimicking more and more an in vivo model is achieved.

DRAWINGS

Figure 4:
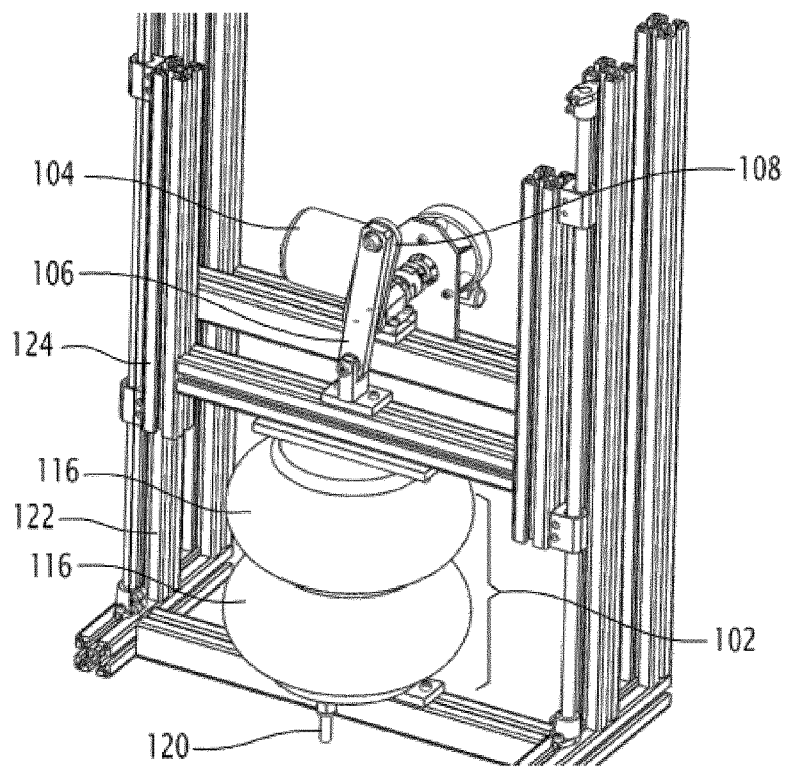

FIG. 4 exemplarily illustrates a first face of the gas pressure system according to various embodiments of the present invention.

Figure 5:
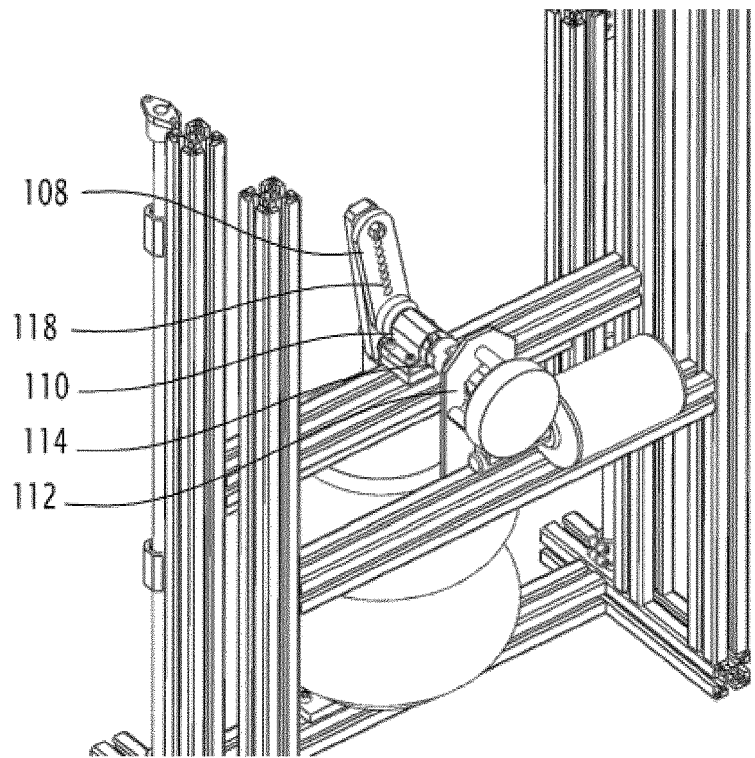

FIG. 5 exemplarily illustrates a second face of the gas pressure system according to various embodiments of the present invention.

Figure 6:
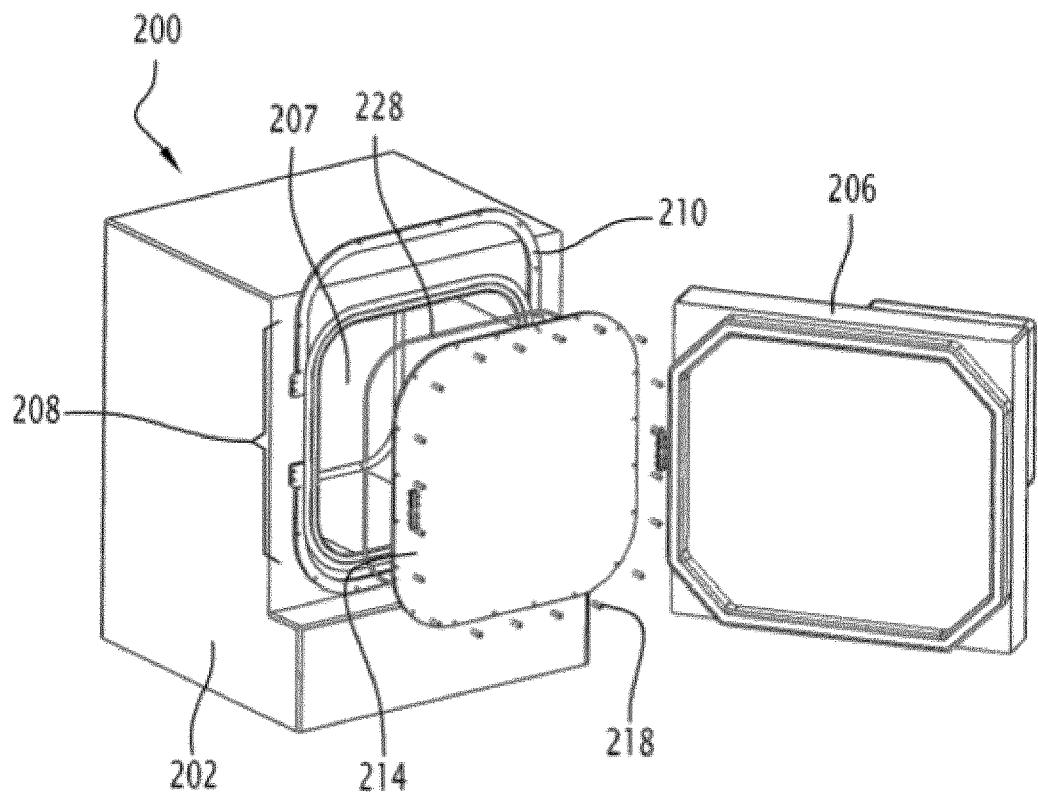

FIG. 6 is an exemplary illustration of a bio-incubator according to various embodiments of the present invention.

Figure 7:
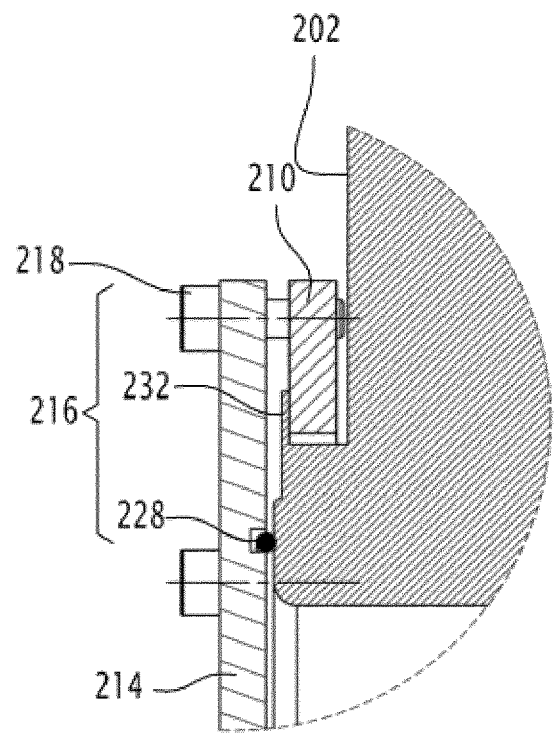

FIG. 7 is a cross-sectional view of the front face of the bio-incubator, in accordance with various embodiments of the present invention.

FIG. 8 is an exemplary illustration of a door of the bio-incubator according to various embodiments of the present invention.

FIG. 9a is a cross-sectional view of the wall of the bio-incubator, in accordance with various embodiments of the present invention.

FIG. 9b is an exemplary view of the traverse on a wall of the bio-incubator, in accordance with various embodiments of the present invention.

Figure 10:
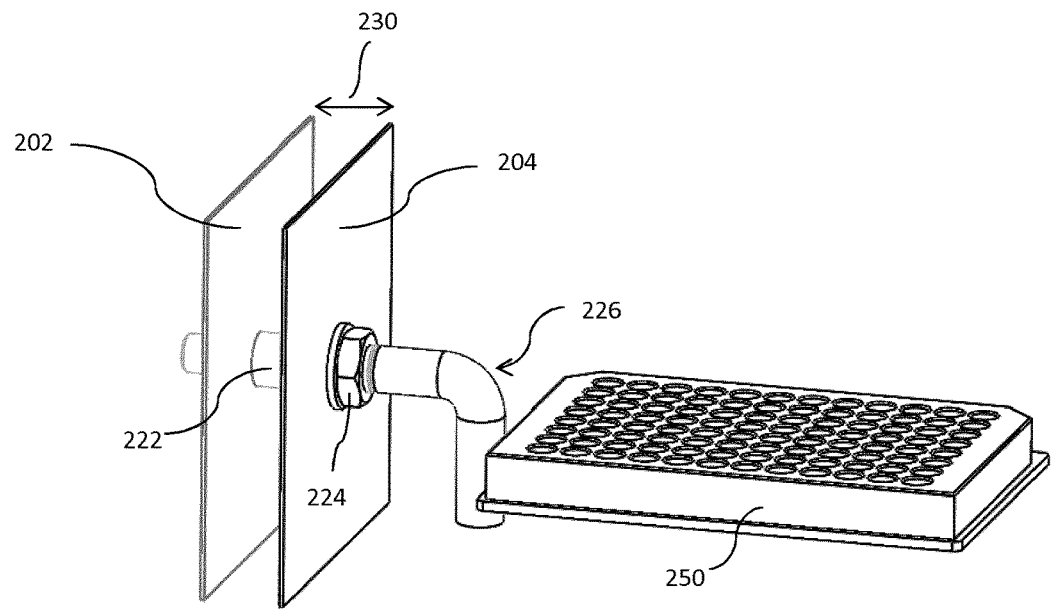

FIG. 10 is an exemplary view of the pipe connected to the traverse of the bio-incubator, in accordance with various embodiments of the present invention.

Figure 11:
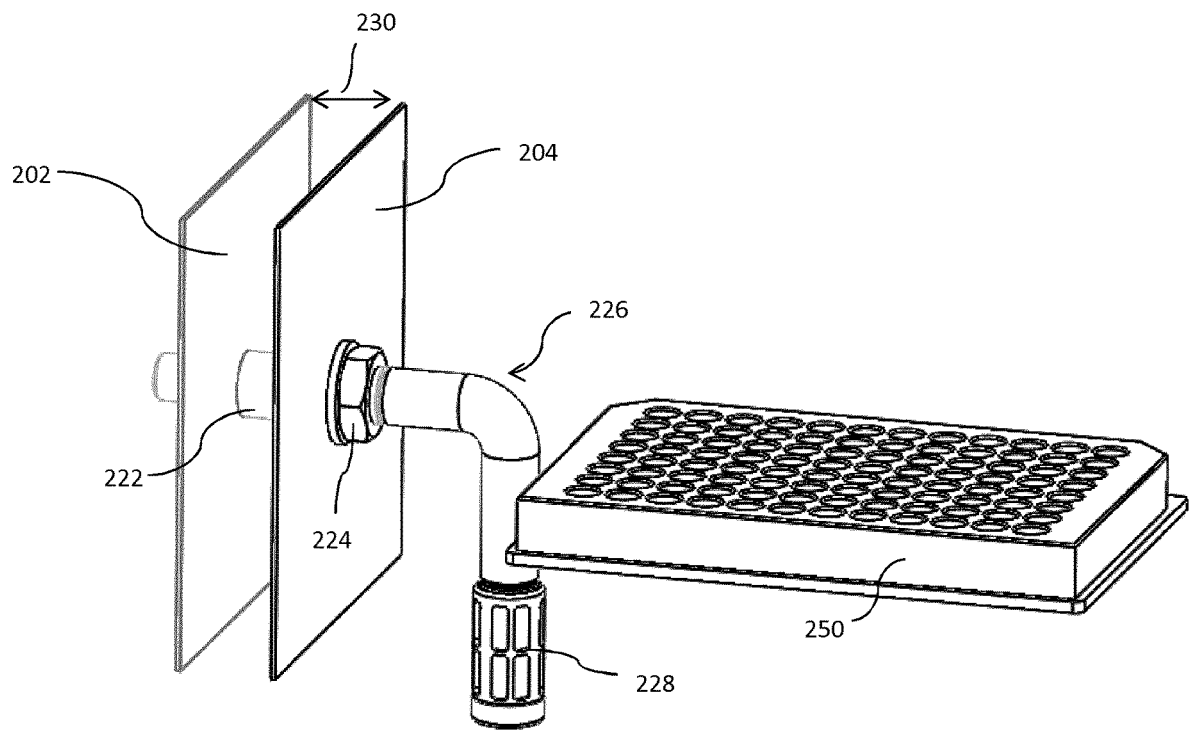

FIG. 11 is an exemplary view of the pipe with a fritted tip, in accordance with various embodiments of the present disclosure.

Figure 12:
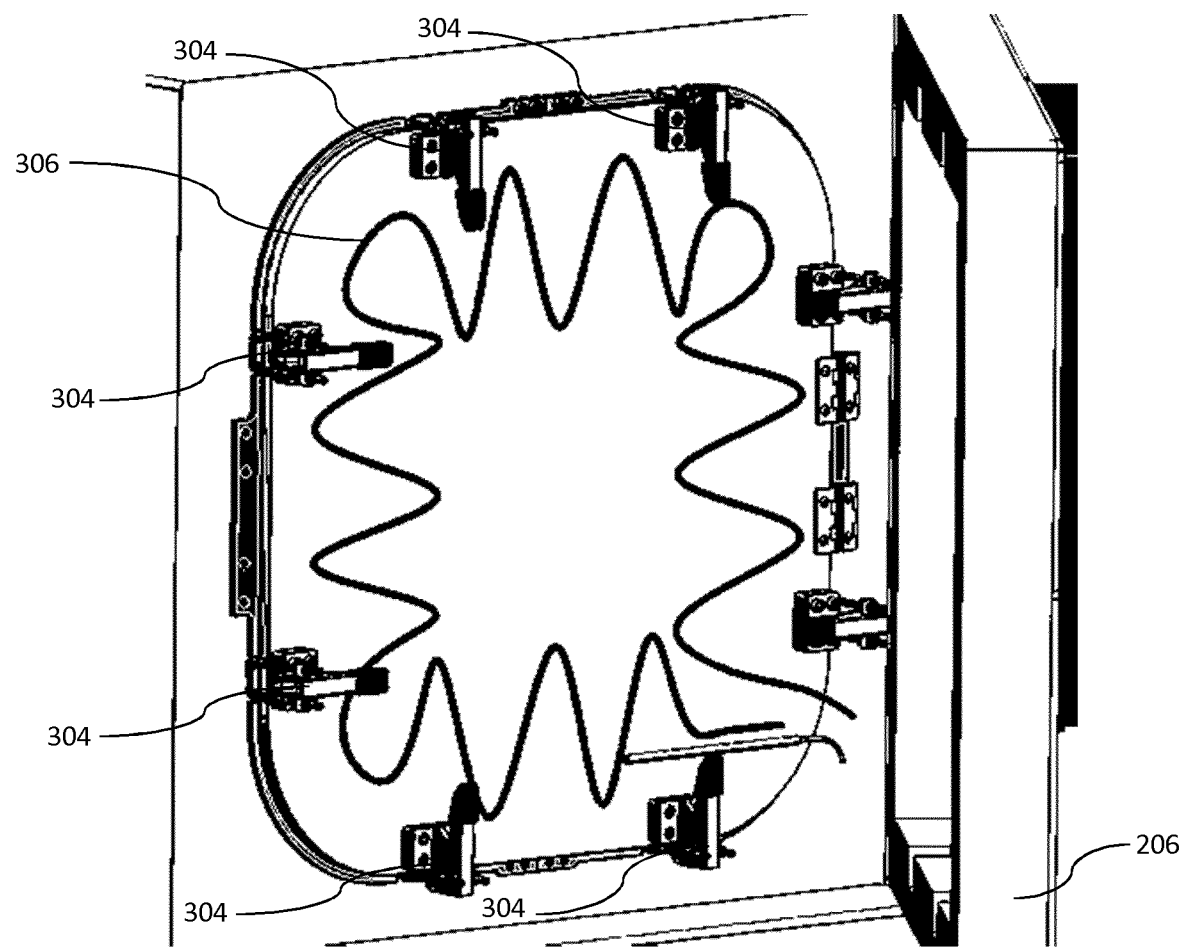

FIG. 12 is and exemplary scheme showing the heating device of the door of the bio-incubator according to various embodiments of the present invention.

DETAILED DESCRIPTION

It is to be understood that the following features disclosed in relation with a particular embodiment can be combined with the features of other embodiments without any restrictions.

Figure 1:
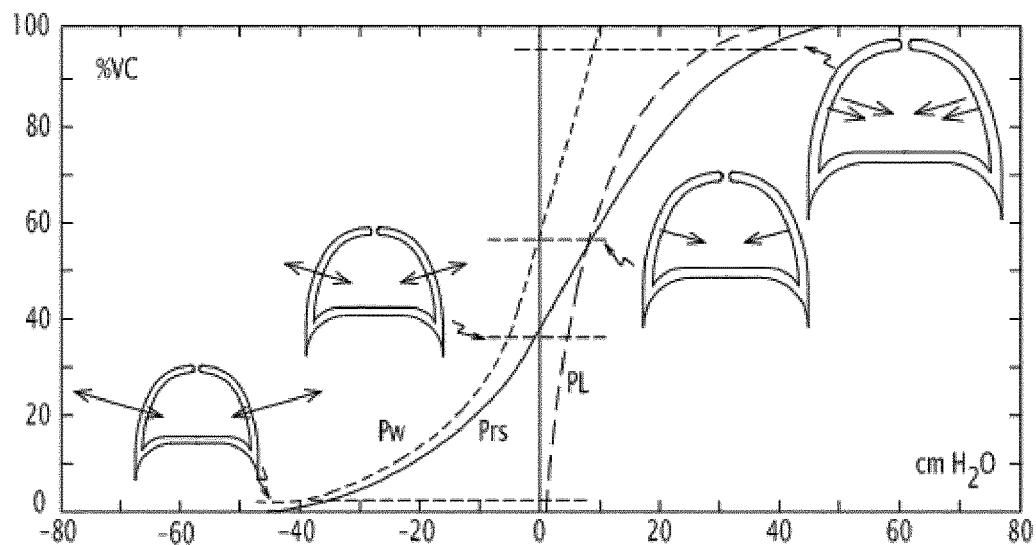
FIG. 1 is an exemplary plot of the vital capacity over the pressure, in accordance with various embodiments of the present invention.
Figure 2:
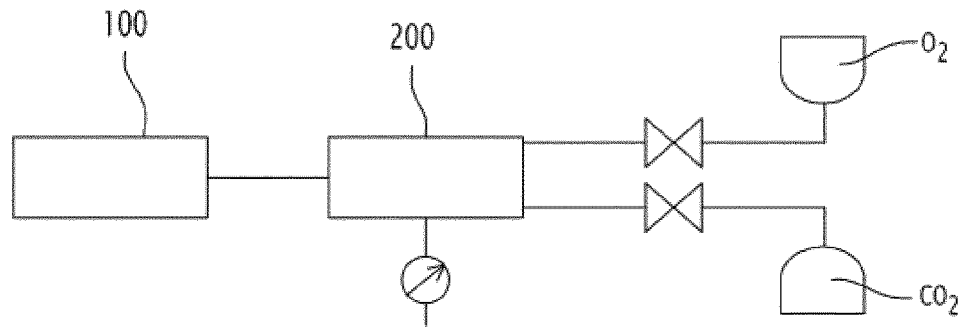
FIG. 2 is an exemplary scheme of the system according to various embodiment of the present invention.

FIG. 2 represents a schematic drawing of the system in accordance with the present invention. A bio-incubator 200, which is optionally in gas connection with $CO_2$ and/or with $O_2$, has been modified to become pressurized and is connected to a gas pressure system 100. A manometer (not shown) has been set up to the bio-incubator 200 in order to control the internal pressure of the bio-incubator 200. The manometer can be a gauge needle, the absence of liquid in this particular type of manometer preventing any variation of humidity level within the bio-incubator 200.

The bio-incubator presents the traditional features of a commercially available bio-incubator. The temperature is adjustable and can be varied from the room temperature (e.g. generally between 20° C. and 25° C.) to higher temperature (e.g. up to 40° C.). The bio-incubator is optionally connected to $CO_2$ and/or $O_2$ and the concentration of those gases can be adjusted. The atmosphere of the bio-incubator can be dry or wet.

In the present invention, such conventional bio-incubator has been modified in order to connect it to a gas pressure system, and to allow the bio-incubator to present air-tight capacities. Those features will be apparent in the rest of the figures and in the following description.

Figure 3:
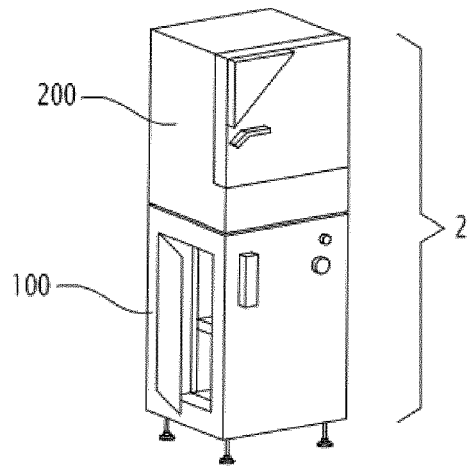
FIG. 3 is an isometric view of the system according to various embodiments of the present invention.

FIG. 3 represents a view of the system 2 in accordance with the present invention. The bio-incubator 200, as modified (in view of its pressurization capabilities) is placed over the gas pressure system 100. A stacking adapter (not shown) might be optionally present above the gas pressure system 100 and the bio-incubator 200. The gas pressure system 100, which is placed below the bio-incubator 200, might optionally comprise feet and/or rollers in order to facilitate the stability and/or displacement of the entire system (2). It has to be understood that the view of FIG. 3 represents only one possible configuration. In other cases (not represented), the bio-incubator might be placed below the gas pressure system or next to the gas pressure system. The bio-incubator and the gas pressure system do not need to be adjacent and might be placed in separate places.

In the following part of the description, the gas pressure system 100 of the present invention will be described.

The gas pressure system is a cyclic gas pressure system since it permits the pressure to vary between a negative pressure (inhalation mode) and a positive pressure (exhalation mode) compared to the atmospheric pressure (1013.25 mbar at sea level). The maximum negative pressure that is reached in the bio-incubator 200 via this cyclic gas pressure system is −100 mbar. The maximum positive pressure that is reached in the bio-incubator 200 via this cyclic gas pressure is +100 mbar.

The sign plus or minus of the pressure corresponds to the pressure flow observed in the bio-incubator.

FIGS. 4 and 5 represent a first and a second face of the cyclic gas pressure system 100 according to the present invention.

The power source of the cyclic gas pressure system 100 is a motor 104. The motor 104 is usually an electric motor.

The motor 104 is coupled to a gear motor 112 and slowly rotates. The coupling to the gear motor 112 allows the transmission of important effort. The rotating movement is transformed into a movement of translation. The effort will be transmitted to a rolling bearing 110 through a coupling member 114 and will actuate a crank mechanism (106, 108) which will confer to the exerted force a sinusoidal scheme.

This mechanical system crank 108-rod 106 is thus used to create the cyclic gas pressure variation, so as to mimic the inhalation and exhalation. In quiet breathing, the respiratory acts are in an amount of 12-15 per minutes. The actuation of the mechanical system have thus an impact on the position of the guiding assembly 124 which is configured for sliding into the frame 122 and consequently compresses and/or expands the volume of the chamber 102. A wall of the chamber 102 is indeed coupled to the guiding assembly 124.

The crank mechanism (106, 108) has an adjustable stroke (movement).

The crank mechanism (106, 108) in various instances comprises a crank 108, or camshaft, which is rotably connected to a rod 106 at an adjustable position along the crank 108.

Advantageously, the chamber 102 is a bellow cylinder, in various instances a bellow cylinder comprising at least two bellows 116.

When the rod 106 is pushed down by the crank 108, the guiding assembly 124 slides downward and compresses the volume of the chamber 102. The air is then pushed out from the outlet 120. This mimics the inhalation mode of the respiration in the bio-incubator 200.

When the rod 106 is pushed up by the crank 108, the guiding assembly 124 slides upward and expands the volume of the chamber 102. The air is then attracted in the chamber 102 from the outlet 120. This mimics the exhalation mode of the respiration in the bio-incubator 200.

The outlet 120 is configured to be in fluid connection with the bio-incubator 200. A pipe can be attached in an air-tight manner in order to achieve the connection of the cyclic gas pressure system 100 and the bio-incubator 200.

The stroke of the crank 108 is in fact adjustable, since several threaded holes 118 are present on the crank. This permits to adjust the volume that will be displaced. In order to permit this variation of volume, at least two threaded holes 118 are necessary. In a way to improve the mechanical control on the variation of volume, nine threaded holes 118 have been established. The crank 108 is thus coupled to one connecting rod 106 in order to transmit the effort onto the chamber 102 via the guiding assembly 124. A simple system of screw and nut is used to couple together the crank 108 and the connecting rod 106.

The crank 108 allows thus to increase and/or to decrease the amount of air to compress and/or to expand.

A control device (not shown) is placed in order to modify and to control the different parameters of the motor 104, such as the rotating speed of the motor 104. This permits the user to have a control of the number of respiratory acts.

In order to mimic quiet breathing, the rotating speed of the motor 104 is slow.

In order to mimic force breathing, the rotating speed of the motor 104 is fast.

In the following part of the description, the bio-incubator 200, modified in accordance with the present invention, will be described.

FIG. 6 shows the bio-incubator 200. The bio-incubator presents an opening 207 necessary to access to the interior of the bio-incubator. The opening 207 is delimited by a doorframe 208 and a door 206 is used to close and/or to open the bio-incubator. The door 206 is in various instances attached to the bio-incubator 200 through two hinges 302. The door 206 can be made in aluminium. This is advantageous with respect to a glass door, because aluminium is a light material (and thus, its thickness and so its resistance to pressure variation, can be increased without a significant increase of weight). An aluminium door can also be regulated in terms of temperature.

The bio-incubator 200 comprises several shelfs (not shown) allows for maximizing the storage space for the wells adapted for cells culture.

The first modification of the bio-incubator in accordance with various embodiments of the present invention consists in sealing the opening 207 in an air-tight manner in order to pressurize the bio-incubator when this one is connected to the cyclic gas pressure system 100.

Consequently, a hermetic cover 214, or a sealing flange, is reversibly fixed to the doorframe 218, so as to completely cover the opening 207 in an air-tight manner.

Air-tight fixation elements 218, such as screw, nut, bolt and/or washer, are used to reversibly fix the hermetic cover 214 to the doorframe 218.

In the specific embodiment shown in FIG. 7, such hermetic cover 214 can be larger than the area of the opening to cover. In such case, the hermetic cover 214 comprises a protruding portion 216, which can be reversibly fixed by the air-tight fixation elements 218 into the external wall 202 of the bio-incubator 200. Optionally, a counter-plate 210 is inserted in one recess 232 that has been designed onto the external wall 202. The protruding portion 216 is then fixed in the counter-plate 210 instead of in the external wall 202.

Advantageously, the hermetic cover 214 is made of stainless steel.

Advantageously, the hermetic cover 214 comprises a hermetic seal 218, in various embodiments an O-ring seal, that fits at least partially or entirely the doorframe 208 of the door 206. The hermetic seal 218 also fits the hermetic cover 214. The hermetic seal 218 is in various instances made of silicone.

As shown on FIG. 8, the door 206 has been further modified in order to prevent any kind of deformation of the inner walls of the bio-incubator 200 due to the pressure variation. The door thickness has been increased in order to avoid such deformation. In various instances, the door thickness is comprised between 5 mm and 15 mm, for example the door thickness is equal to 8 mm.

A fasten mechanism, comprising at least one lock 304, can be disposed along the doorframe 208, or in various instances on the hermetic cover 214. It can be established in order to hermetically seal the door 206 to the bio-incubator 200. The fasten mechanism can be composed of two locks on the part of the doorframe 208 (or the hermetic cover 204) which is opposed to the part of the doorframe 208 bearing the hinges 302 of the door 206.

Two further locks can be disposed on the top and below part of the doorframe 208.

With this fasten mechanism, when the door 206 is closed, the door is literally pressed onto the doorframe 208, or in various instances onto the hermetic cover 214, in order to provide a homogenous airtight seal between the door 206 and the bio-incubator 200.

Still in order to prevent the deformation due to the cyclic variation of internal pressure, a rigid stainless steel frame has been placed inside the bio-incubator 200. The steel frame presses on the inside walls of the incubator, preventing them from deforming, which would cause unwanted fluctuation of the internal pressure.

This frame allows for the original shelfs of the bio-incubator 200 to remain inside. They only reinforce the inside walls of the bio-incubator.

The second modification of the bio-incubator in accordance with various embodiments the present invention consists in providing an air-tight connection between the bio-incubator 200 and the cyclic gas pressure system 100 (see FIGS. 9a and 9b).

An orifice 220 has thus been made in one of the walls of the bio-incubator 200. The orifice 220 is configured to be in fluid connection with the cyclic gas pressure system 100. The orifice 200 is made through the external wall 202 and the internal wall 204 of the bio-incubator and traverses therefore the zone 230, which is between the external wall 202 and the internal wall 204. The zone 230 can be thermally insulated in order to keep the inner temperature of the bio-incubator 200 constant.

The orifice 220 comprises an air-tight traverse 222, or a feedthrough, which is fastened to the external wall 202 and to the internal wall 202 by air-tight fixation elements 224, such as screw, nut, bolt and/or washer. As shown by FIG. 9A, the air-tight fixation elements 224 can be disposed on the external wall 202 side and/or the internal wall 204 side.

Advantageously, the air-tight traverse 222 or feedthrough is made of stainless steel.

In order to incubate one or more cells and/or to perform organotypic culture (growing cells in a tridimensional environment) for biological investigation, the bio-incubator 200 is equipped with at least one bowl 250 or at least one plate, such as one 6-well cell culture plate. Such bowl 250 can contain a fluid growth medium and that can act as a reservoir for one or more wells (generally 6 wells) designed for hosting one or more cells. The surface of the well is inferior or equal to 5 cm$^2$.

One example of bowl 250 (comprising more than 6 wells) is shown on FIGS. 10 and 11.

The at least one bowl 250 is in various instances being placed on the shelf of the bio-incubator 200.

The air-tight traverse 222 or feedthrough is advantageously connected to a pipe 226 configured to prevent the drying-up of the cells, as shown on FIG. 10. In other words, the air-tight traverse 222 or feedthrough comprises a pipe (226) configured to deviate the air influx from the one or more cells and/or organotypic culture. For instance, the pipe 226 is thus advantageously curved toward the top part of the bio-incubator 200 (not shown on FIG. 10) or the bottom part of the bio-incubator 200 (as shown on FIG. 10). The pipe can also be curved toward the inner wall 204 of the bio-incubator 200 (not shown) or in any direction that is not towards the cultured cells. As the air flux is not directed toward the wells adapted for cells culture, this prevents the cultured cells to become dried-up. This way of directing the air flux is very important, since important influx and efflux are provided inside the bio-incubator 200 in contact with several cells that are expected to grow and develop.

FIG. 11 shows a fritted tip 228 of the pipe 226. This fritted tip 228 allows for enhancing the decreasing of the air flux within the bio-incubator and therefore participates to prevent the drying-up of the cells and/or tissues that are cultured. The fritted tip 228 can be a silencer (from Festo Company, for instance).

When in function, the system 2 of the present invention thus consists in the bio-incubator 200 filled with the lung cells in a well, hermetically connected to the cyclic gas pressure system 100. The system 2 is airtight, notably due to the hermetic cover 214 and the air-tight fixation elements 218 and 224. A source of oxygen and/or carbon dioxide might be connected to the bio-incubator 200 without changing the internal pressure of the hermetic system 2. One or several analytical instruments might be placed inside the incubator 200 in order to monitor the behaviour of the cell, the cells and/or the organotypic cultures under respiration conditions implemented by the cyclic gas pressure system 100.

In another embodiment of the present invention, the system 2 of the present invention can be coupled to a system, which comprises exposure means for exposing aerosol to one or more cells. By aerosol, it is to be understood a colloidal suspension of microparticles and/or nanoparticles dispersed in air and/or a gas.

An example of a commercially available system used for delivering aerosol to one or more cells is the Vitrocell® exposure system.

In another embodiment of the present invention, the humidity inside the bio-incubator 200 can be regulated. The bio-incubator can thus be regulated to be at a temperature comprised between 35° C. and 39° C., in various instances between 36° C. and 38° C. In particular, the bio-incubator 200 can be regulated to be at a temperature of 37° C. The temperature can be usually controlled by a main controller (not represented), which can be a computer.

A heating device 306 can thus be placed within the door, as shown in FIG. 12. The heating device 306 can be for example an electrical resistance. This heating device 306 can be advantageously placed within the door since the door has been made in a compatible material (e.g. aluminium).

By regulating and maintaining the temperature in a homogenous manner throughout the whole bio-incubator, any problems resulting from condensation can be avoided.

Similarly, the chamber 102 has been modified to be kept at the same temperature as inside the bio-incubator, namely at a temperature comprised between 35° C. and 39° C., in various instances between 36° C. and 38° C. In particular, the chamber 102 can be modified to be at a temperature of 37° C.

This is in practice achieved by silicone rubber heating elements that are covering the chamber 102. These are surface heaters ideal where precise heating (e.g. 37° C.) is required. Silicone rubber provides high temperature tolerance and high insulating properties.

Those silicone rubber heating elements can also be reinforced with fiberglass for obtaining greater mechanical strength.

Those silicone rubber heating elements can be positioned on the flat part of the bellows 116.

Those silicon rubber heating elements can also be electrically connected to the electrical system of the bio-incubator 200, the electrical system being part of a main controller of the bio-incubator 200.

The invention claimed is:

1. A system for incubating one or more cells and organotypic cultures for biological investigation and toxicology assessment, said system comprising:
a bio-incubator with at least one orifice;
a pressure system fluidly connected with the bio-incubator through the at least one orifice;
wherein the bio-incubator and the gas pressure system form a hermetically closed circuit;
wherein the pressure system is a cyclic gas pressure system configured for cyclically varying the gas pressure in the bio-incubator between a negative pressure of at least −1 mbar and a positive pressure of at least +1 mbar compared to the atmospheric pressure, so as to reproduce the pressure conditions in lungs of a living mammal; and the orifice comprises a feedthrough with a pipe comprising inside the bio-incubator a portion curved towards a bottom part or a top part of the bio-incubator configured to deviate the air influx from the one or more cells and/or organotypic cultures, the curved portion terminating with a silencer for decreasing the air influx within the bio-incubator.

2. The system according to claim 1, wherein the silencer is a fritted tip.

3. The system according to claim 1, wherein the feedthrough is an air-tight traverse.

4. The system according to claim 1, wherein the gas pressure in the bio-incubator is within a range comprised between −100 mbar and +100 mbar.

5. The system according to claim 1, wherein the hermetically closed circuit further comprises an openable connection to at least one gas source.

6. The system according to claim 1, wherein the bio-incubator comprises at least one well adapted for cell cultures.

7. The system according to claim 1, wherein the cyclic gas pressure system comprises a chamber with a volume that can be varied by an actuator, the chamber comprising at least one outlet in fluid connection with the bio-incubator.

8. The system according to claim 7, wherein the system comprises a guiding assembly slidably mounted on the chamber and movable by the actuator, a wall of the chamber being coupled to the guiding assembly.

9. The system according to claim 7, wherein the chamber is a bellow cylinder.

10. The system according to claim 7, wherein the chamber is at least partially covered with heating elements.

11. The system according to claim 7, wherein the actuator comprises a motor and a crank mechanism for reciprocally varying the volume of the chamber.

12. The system according to claim 11, wherein the crank mechanism has an adjustable stroke and comprises a crank rotatably connected to a rod at an adjustable position along the crank.

13. The system according to claim 1, wherein the bio-incubator comprises:
an opening delimited by a doorframe;
a door for closing the opening; and
a hermetic cover being mounted between the door and the opening;
wherein the hermetic cover is designed for being airtightly fixed by air-tight fixation elements to the doorframe; and
wherein the bio-incubator further comprises a wall with an orifice configured to be in fluid connection with the cyclic gas pressure system.

14. The system according to claim 13, wherein the door comprises a heating device, the heating device being disposed inside the door.

15. The system according to claim 14, wherein the heating device an electrical resistance.

16. The system according to claim 13, wherein the hermetic cover comprises a protruding portion designed for being air-tightly fixed by the air-tight fixation elements to the doorframe of the bio-incubator through a counter-plate which is placed on the external wall of the bio-incubator at least partially around the doorframe, the counter-plate being inserted into a recess disposed on the doorframe.

17. The system according to claim 13, wherein the hermetic cover comprises a hermetic seal that fits with the doorframe of the door and the hermetic cover, the hermetic seal being made of elastomer.

18. The system according to claim 13, wherein the orifice traverses a zone between an external wall and an internal wall of the bio-incubator, and comprises an air-tight traverse fastened to the external wall and to the internal wall by air-tight fixation elements.

19. A device for analysing the effect of aerosol of nanoparticles on one or more cells, said device comprising:
a first system comprising exposure means for exposing aerosol to one or more cells; and
a second system for incubating at least one of one or more cells and organotypic cultures for biological investigation and toxicology assessment, wherein said second system comprises:
a bio-incubator with at least one orifice; and
a pressure system fluidly connected with the bio-incubator through the at least one orifice;
wherein the bio-incubator and the gas pressure system form a hermetically closed circuit, and
wherein the pressure system is a cyclic gas pressure system configured for cyclically varying the gas pressure in the bio-incubator between a negative pressure of at least −1 mbar and a positive pressure of at least +1 mbar compared to the atmospheric pressure, so as to reproduce the pressure conditions in lungs of a living mammal, and
the orifice comprises a feedthrough with a pipe comprising inside the bio-incubator a portion curved towards a bottom part or a top part of the bioincubator configured to deviate the air influx from the one or more cells and/or organotypic cultures, said curved portion terminating with a silencer for decreasing the air influx within the bio-incubator.

* * * * *